(12) United States Patent
Barry (10) Patent No.: US 9,594,058 B2
(45) Date of Patent: Mar. 14, 2017

(54) IMPLEMENTING STEEP DELTA WAVE TECHNIQUE TO INSPECT JOINTS

(71) Applicant: Bell Helicopter Textron Inc., Fort Worth, TX (US)

(72) Inventor: Robert James Barry, Arlington, TX (US)

(73) Assignee: BELL HELICOPTER TEXTRON INC., Fort Worth, TX (US)

( * ) Notice: Subject to any disclaimer, the term of this patent is extended or adjusted under 35 U.S.C. 154(b) by 246 days.

(21) Appl. No.: 14/500,218

(22) Filed: Sep. 29, 2014

(65) Prior Publication Data

US 2016/0091463 A1    Mar. 31, 2016

(51) Int. Cl.
*G01N 29/04* (2006.01)
*G01N 29/11* (2006.01)
*G01N 29/22* (2006.01)
*G01B 17/02* (2006.01)
*G01M 13/00* (2006.01)
*G01N 29/24* (2006.01)

(52) U.S. Cl.
CPC ............. *G01N 29/04* (2013.01); *G01B 17/02* (2013.01); *G01M 13/00* (2013.01); *G01N 29/11* (2013.01); *G01N 29/221* (2013.01); *G01N 29/2487* (2013.01); *G01N 2291/048* (2013.01); *G01N 2291/055* (2013.01); *G01N 2291/056* (2013.01); *G01N 2291/267* (2013.01); *G01N 2291/269* (2013.01)

(58) Field of Classification Search
CPC .... G01N 29/11; G01N 29/2487; G01N 29/04; G01N 29/221; G01N 2291/048; G01N 2291/055; G01N 2291/056; G01N 2291/267; G01N 2291/269; G01B 17/02; G01M 13/00
USPC .......................................................... 73/632
See application file for complete search history.

(56) References Cited

U.S. PATENT DOCUMENTS

| 2,545,309 | A | 3/1951 | Roberts |
| 3,712,119 | A | 1/1973 | Cross et al. |
| 3,895,685 | A | 7/1975 | Gillette et al. |
| 4,174,636 | A | 11/1979 | Pagano |

(Continued)

FOREIGN PATENT DOCUMENTS

| DE | 10014936 | 10/2001 |
| DE | 102004030154 | 2/2006 |

OTHER PUBLICATIONS

Communication Pursuant to Article 94(3) EPC issued in European Application No. 15150844.7 on Feb. 11, 2016; 5 pages.

(Continued)

*Primary Examiner* — J M Saint Surin (57) ABSTRACT

One aspect of a process of inspecting a joint that connects two parts includes directing an ultrasonic beam from an ultrasonic beam transmitter at a joint that connects two parts, the ultrasonic beam forming an angle between at least 14 degrees and at most 21 degrees with a joint axis of the joint, wherein the ultrasonic beam passes through a joint thickness of the joint. The process also includes determining a quality of the joint based, in part, on a difference between a strength of the ultrasonic beam directed at the joint and a strength of a portion of the ultrasonic beam that passed through the joint thickness.

20 Claims, 7 Drawing Sheets

(56) References Cited

U.S. PATENT DOCUMENTS

| | | | | |
|---|---|---|---|---|
| 4,265,119 A * | 5/1981 | Dubetz | ............ | G01N 29/11 |
| | | | | 73/588 |
| 6,920,791 B2 * | 7/2005 | Wagner | ............ | G01N 29/221 |
| | | | | 73/620 |
| 7,204,147 B2 * | 4/2007 | Fujimoto | ............ | G01N 29/11 |
| | | | | 73/598 |
| 7,775,415 B2 * | 8/2010 | Maev | ............ | G01N 29/262 |
| | | | | 219/91.1 |
| 8,091,426 B2 * | 1/2012 | Komatsu | ............ | G01N 29/04 |
| | | | | 73/602 |
| 9,010,186 B2 * | 4/2015 | Pagano | ............ | G01N 29/04 |
| | | | | 73/636 |
| 2003/0154801 A1 | 8/2003 | Georgeson | | |
| 2005/0126294 A1 * | 6/2005 | Bossi | ............ | G01N 29/11 |
| | | | | 73/629 |
| 2007/0068907 A1 * | 3/2007 | Batzinger | ............ | B23K 11/252 |
| | | | | 219/109 |
| 2009/0283569 A1 * | 11/2009 | Ramaswamy | ............ | B23K 11/252 |
| | | | | 228/1.1 |

OTHER PUBLICATIONS

European Search Report issued in European Application No. 15150844.7 on Jul. 21, 2015; 4 pages.

Communication Pursuant to Article 94(3) EPC issued in European Application No. 15150844.7 on Aug. 7, 2015; 6 pages.

Cosgrove, Don, "Check-Out" of the Delta Technique, DP70-001, Oct. 19, 1970, 42 pages.

Office action issued in Canadian Application No. 2,905,120 on Aug. 1, 2016, 4 pages.

* cited by examiner

| Decibels | Size | Area ratio |
|---|---|---|
| 16 | .060" | 6.31 to 1 |
| 14 | .056" | 5.01 to 1 |
| 12 | .050" | 4 to 1 |
| 10 | .044" | 3.16 to 1 |
| 8 | .040" | 2.51 to 1 |
| 6 | .035" | 2 to 1 |
| 4 | .031" | 1.58 to 1 |
| 2 | .028" | 1.26 to 1 |
| 0 | .025" | 1 to 1 |
| -2 | .022" | 0.79 to 1 |
| -4 | .020" | .063 to 1 |
| -6 | .018" | 0.5 to 1 |
| -8 | .016" | 0.4 to 1 |

IMPLEMENTING STEEP DELTA WAVE TECHNIQUE TO INSPECT JOINTS

TECHNICAL FIELD

This disclosure relates to implementing a steep delta wave technique for ultrasonic inspection of a joint, e.g., a joint joining parts of an aircraft.

BACKGROUND

In many industries, joints joining separate parts together into a single component are inspected for defects before the component is installed. The joints can be inspected using ultrasonic techniques. For example, a joint in a component for use in an aircraft can be inspected for defects using an ultrasonic beam transmitter and ultrasonic receiver. The ultrasonic beam transmitter directs an ultrasonic beam through the joint and the ultrasonic receiver receives ultrasonic signals passed through the part. The ultrasonic signals received by the ultrasonic receiver can be analyzed to inspect the joint.

SUMMARY

This disclosure describes technologies relating to inspecting joints with steep delta wave ultrasonic techniques.

Certain aspects of the subject matter described here can be implemented as a method of inspecting a joint that connects two parts. The method includes directing an ultrasonic beam from an ultrasonic beam transmitter at a joint that connects two parts, the ultrasonic beam forming an angle between at least 14 degrees and at most 21 degrees with a joint axis of the joint, wherein the ultrasonic beam passes through a joint thickness of the joint. The method also includes determining a quality of the joint based, in part, on a difference between a strength of the ultrasonic beam directed at the joint and a strength of a portion of the ultrasonic beam that passed through the joint thickness.

This, and other aspects, can include one or more of the following features. The joint can have a rectangular width. Directing the ultrasonic beam at the joint can include directing the ultrasonic beam at a first edge of the rectangular width of the joint and traversing the ultrasonic beam from the first edge to a diagonally opposite edge of the joint. Directing the ultrasonic beam at the joint can include directing the ultrasonic beam at multiple locations on the joint. The method can also include determining multiple strengths of the ultrasonic beam at the respective multiple locations on the joint and determining multiple strengths of multiple portions of the ultrasonic beam, each portion having passed through the joint thickness at a respective location on the multiple locations. Determining the quality of the joint can include identifying a region in the joint through which the ultrasonic beam directed at multiple locations passed and determining a quality of the identified region in the joint based, in part, on a difference between a strength of the ultrasonic beam directed at the location and a strength of a portion of the ultrasonic beam that passed through the joint thickness at the location. Determining the quality of the joint can include identifying a defect in the joint based on the difference between the strength of the ultrasonic beam directed at the joint and the strength of the portion of the ultrasonic beam that passed through the joint thickness. Determining the quality of the joint can include determining a depth of the defect in the joint. Determining the quality of the joint can also include identifying a first defect and a second adjacent defect along a width of the joint based on the difference between the strength of the ultrasonic beam directed at the joint and the strength of the portion of the ultrasonic beam that passed through the joint thickness. Determining the quality of the joint can include determining a spacing between the first defect and the second adjacent defect. Determining the quality of the joint can include performing multiple scans on the ultrasonic beam and the portion of the ultrasonic beam that passed through the joint and determining the quality of the joint based, in part, on an output of the multiple scans. The joint can be an electron beam weld. The joint can join a spiral bevel gear of a rotorcraft to a shaft of the rotorcraft. The method can include calibrating the ultrasonic beam transmitter relative to the joint before directing the ultrasonic beam at the joint. The angle can be at least one of 15 degrees or 16 degrees. The frequency of the ultrasonic beam directed at the joint can be at least 10 MHz.

Certain aspects of the subject matter described here can be implemented as a joint inspection system. The system includes an ultrasonic beam transmitter, the ultrasonic beam transmitter operable to direct an ultrasonic beam at a joint that connects two parts. The ultrasonic beam forms an angle between at least 14 degrees and at most 21 degrees with a joint axis of the joint, and the ultrasonic beam passes through a joint thickness of the joint. The system also includes an ultrasonic beam receiver.

This, and other aspects, can include one or more of the following features. The ultrasonic beam transmitter can be arranged relative to the joint to direct the ultrasonic beam at a first edge of the rectangular width of the joint and traverse the ultrasonic beam from the first edge to a diagonally opposite edge of the joint. The system can also include a computer system storing instructions executable by the computer system to determine a quality of the joint based, in part, on a difference between a strength of the ultrasonic beam directed at the joint and a strength of a portion of the ultrasonic beam that passed through the joint thickness. Directing the ultrasonic beam at the joint can include directing the ultrasonic beam at multiple locations on the joint. Determining the quality of the joint can include determining multiple strengths of the ultrasonic beam at the respective multiple locations on the joint and determining multiple strengths of multiple portions of the ultrasonic beam, each portion having passed through the joint thickness at a respective location of the multiple locations. Determining the quality of the joint can also include identifying a region in the joint through which the ultrasonic beam directed at a location of the multiple locations passed. Determining the quality of the joint can also include determining a quality of the identified region in the joint based, in part, on a difference between a strength of the ultrasonic beam directed at the location and a strength of a portion of the ultrasonic beam that passed through the joint thickness at the location. Determining the quality of the joint can also include identifying a defect in the joint based on the difference between the strength of the ultrasonic beam directed at the joint and the strength of the portion of the ultrasonic beam that passed through the joint thickness. Determining the quality of the joint can also include determining a depth of the defect in the joint. Determining the quality of the joint can include identifying a first defect and a second adjacent defect along a width of the joint based on the difference between the strength of the ultrasonic beam directed at the joint and the strength of the portion of the ultrasonic beam that passed through the joint thickness. Determining the quality of the joint can include determining a spacing between the first defect and the second adjacent defect. Determining the quality of the joint can include performing multiple scans on the ultrasonic beam and the portion of the ultrasonic beam that passed through the joint. Determining the quality of the joint can be based, in part, on an output of the multiple scans.

The details of one or more implementations of the subject matter described in this disclosure are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

This disclosure relates to the inspection of joints using steep delta wave ultrasonic techniques. A joint joins two separate parts together into a single component. In some cases, joints are inspected for defects, e.g., during a manufacturing process, prior to installation, during periodic maintenance or overhaul, in response to failure, or at other times. For example, a joint formed by welding two metal parts can have defects or anomalies in or around the weld that are not obvious or that are internal to the joint, such as porosity, voids, lack of fusion, cold shuts, corrosion, cracking, combinations of them or other defects. The joint can be inspected using ultrasonic techniques that can detect internal or unobvious defects. In some cases, the joint is inspected by directing an ultrasonic beam at an angle relative to a joint axis, for example at 22-23 degrees relative to a joint axis. When the beam inside the joint reaches an internal anomaly, the ultrasonic energy can be scattered and detected by an ultrasonic receiver. The use of an angled ultrasonic beam is sometimes referred to as the "delta wave technique."

In some cases, the parts are sized or designed such that the inspection system can completely inspect the joint. The joined parts can have substantially smooth and have substantially parallel sides in the region around the joint. For example, the component surfaces on either side of the joint may can be flat for a length proportional to the joint thickness (e.g. twice the thickness of the joint). In some cases, the ultrasonic beam can be traversed or indexed along a dimension of the joint to inspect the entire joint. In some cases, the parts can have a larger-than-needed dimension (e.g., around the region of the joint) to enable the entire joint to be inspected. Adding length (or other dimension) to a part can also add length (or corresponding dimension) to related parts, such as gears that interact with the component or a housing that encloses the component. For an example component of a spiral bevel gear in a gearbox, a gear that interacts with the spiral bevel gear can have larger diameter or a longer shaft length to accommodate the larger size of the spiral bevel gear. Thus, increasing part dimensions can increase cost and weight to the entire system. In an application such as an aircraft that includes several inter-connected parts, additional weight, e.g., to accommodate inspection systems, can increase fuel consumption and reduce operational efficiency.

This disclosure describes a process for inspecting a joint using an ultrasonic beam. The inspection process can be used to determine a quality of a joint by inspecting the joint for defects such as porosity, voids, damage, the presence of foreign objects, combinations of them, or other defects. An ultrasonic beam transmitter directs an ultrasonic beam at the joint, forming an angle between the ultrasonic beam and a joint axis of the joint. Directing the ultrasonic beam at the joint at a steep angle (e.g. less than 22 degrees with respect to the joint axis) causes the beam to refract into the joint at a steep angle. In the present disclosure, the ultrasonic beam is directed at the joint at an angle between at least 14 degrees and at most 21 degrees with a joint axis of the joint. For example, the beam can be directed at an angle of 15 degrees, 16 degrees, or another angle with respect to the joint axis. In some cases, a steep beam needs less part length on either side of the joint to completely inspect the joint. A part with a smaller size can reduce the size and weight of the system. For example, a shorter transmission shaft in a rotorcraft can reduce the distance needed from the rotors to the engine and thus reduce the overall size and weight of the rotorcraft, and, in turn, fuel consumed to operate the rotorcraft.

Figure 1:
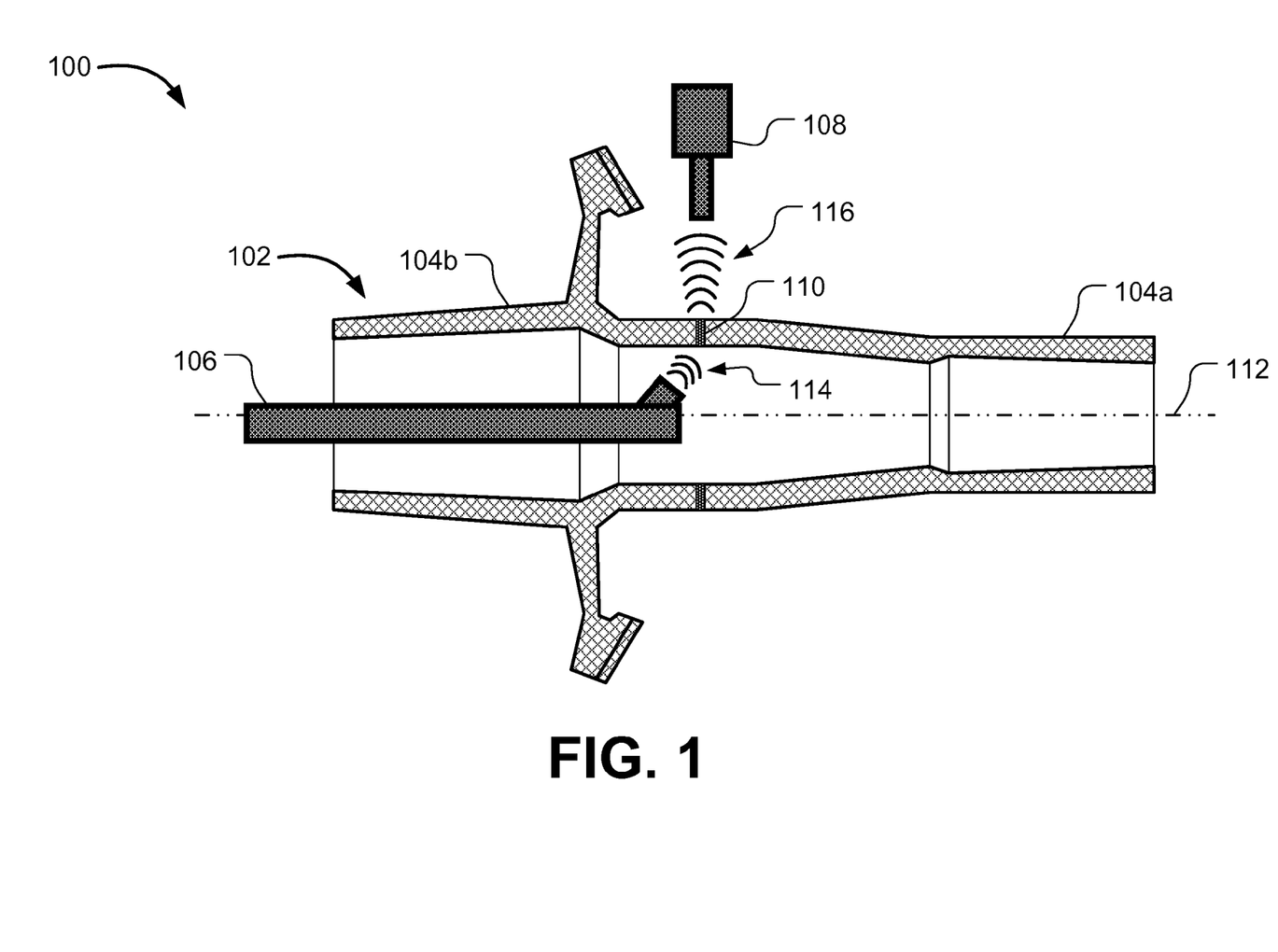
FIG. 1 shows a schematic of an example inspection system for inspecting a joint in a component.
Figure 2:
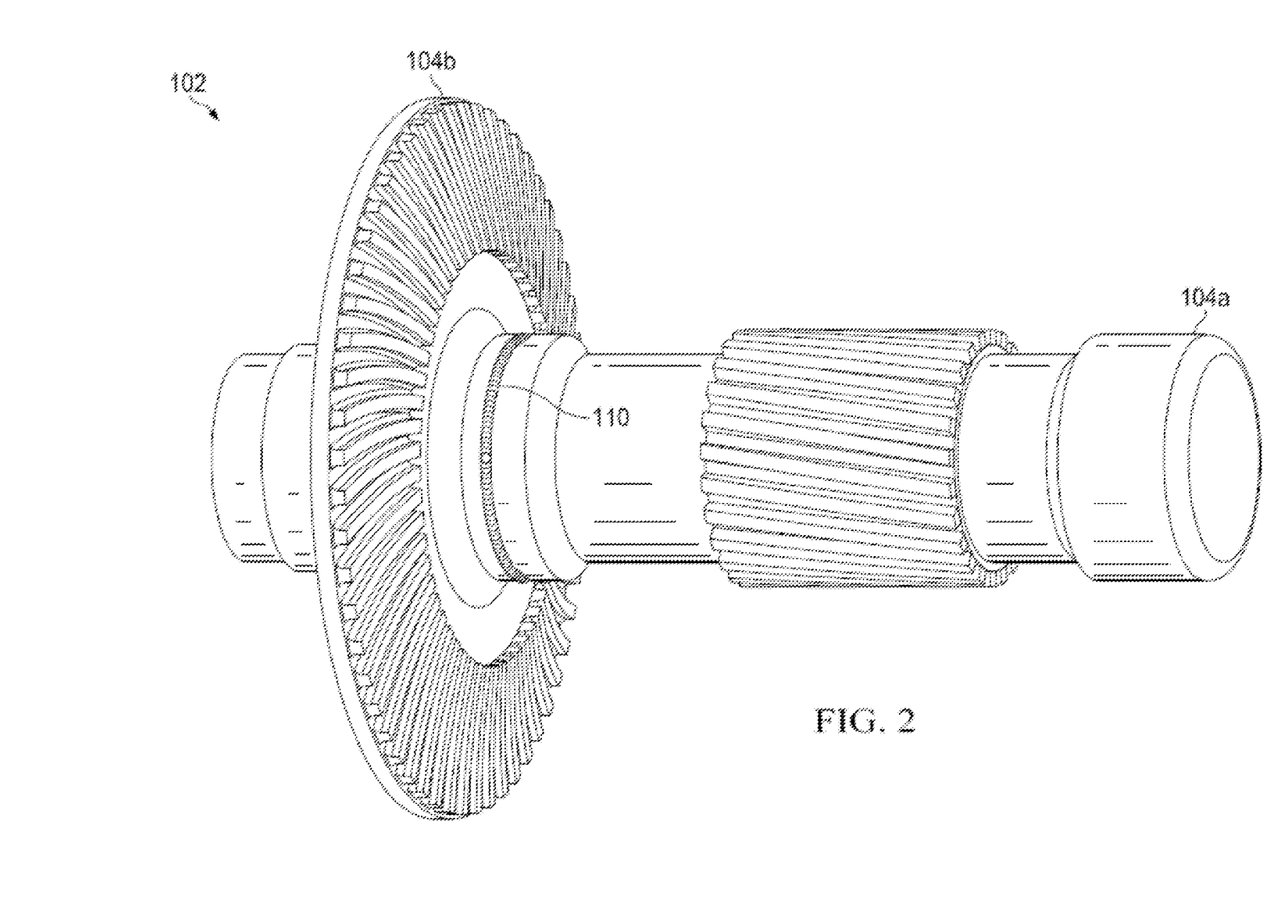
FIG. 2 shows a schematic of example parts joined into a single example component at a joint.

FIG. 1 shows an example inspection system 100 for inspecting a joint 110 in an example component 102. FIG. 1 shows a cross-sectional view of first part 104a and second part 104b joined into single example component 102 at joint 110. FIG. 2 shows an oblique view of parts 104a and 104b joined into the single example component 102 at joint 110. In FIG. 1 and FIG. 2, first part 104a is a shaft in a rotorcraft, and second part 104b is a spiral bevel gear in a rotorcraft. Parts 104a and 104b are example parts; the parts can be other types of parts such as gears, shafts, stiffeners, linkages, housings, piping, or other parts. The parts 104a and 104b can be metallic parts, composite parts, or parts made of another material. In some cases, more than two parts are joined together to form a single component, and more than one joint is used to join the parts. The inspection system 100 can be used to inspect multiple joints on a single component. In some implementations, the component 102 is rotated about a component axis 112 during inspection.

The inspection system 100 could be used to inspect joints used in aircraft applications such as fixed-wing aircraft, tiltrotor aircraft, rotorcraft, or other aircraft. The inspection system 100 could also be used to inspect joints used in other applications such as automotive systems (e.g. automobiles, ATVs, motorcycles, or other automotive systems), submersible systems, marine systems (e.g. personal watercraft, boats, or other marine systems), agricultural systems (e.g. tractors or other agricultural systems), power equipment (e.g. generators, lawn mowers, or other power equipment), construction equipment (e.g. industrial vehicles, heavy machinery, or other equipment), or other systems.

In some implementations, the inspection system 100 includes an example ultrasonic beam transmitter 106 and an example ultrasonic receiver 108. The ultrasonic beam transmitter 106 is directed toward a first location of the joint 110, and the ultrasonic receiver 108 is directed at a second location of the joint 110. The transmitter 106 and receiver 108 can be directed to other separate locations on the joint 110, such as locations on opposing sides of the joint 110, adjacent locations on the joint 110, or other locations on the joint 110. For example, the transmitter 106 can be directed toward a location on one end of the joint 110, and the receiver 108 can be directed toward a location on the opposite end of the joint 110. In some implementations, the ultrasonic beam transmitter 106 and the component 102 are submerged or partially submerged in a fluid such as water, oil, or another fluid. Some fluids (such as water) can transmit ultrasonic energy more readily and with less loss than air. The ultrasonic beam transmitter 106 can include one or more ultrasonic transducers, piezoelectric transducers, or other types of ultrasonic elements that generate ultrasonic energy. In some cases, the ultrasonic beam transmitter 106 includes multiple ultrasonic elements in phased array. The ultrasonic beam transmitter 106 can direct an ultrasonic beam 114 with a frequency such as 10 MHz, 20 MHz, or another frequency. The ultrasonic beam transmitter 106 directs an ultrasonic beam 114 at a location on the joint 110. A portion of the ultrasonic beam 114 is transmitted through the joint 110. A second portion of the ultrasonic beam may be scattered by defects, and a portion of the scattered beam is transmitted through the joint 110.

The ultrasonic receiver 108 can include one or more ultrasonic transducers such as piezoelectric transducers or other types of transducers. The ultrasonic receiver 108 receives ultrasonic signals 116 passed through the location of the joint that can be used to inspect the joint 110. For example, the ultrasonic signals 116 can be portions of the ultrasonic beam 114 that have scattered from the joint 110. The ultrasonic transmitter 106 can be sequentially directed at multiple adjacent locations on the joint 110, and the receiver 108 can receive portions of the scattered beam for each respective location. For example, the ultrasonic transmitter 106 can be indexed along the part length perpendicular to the joint 110 and the ultrasonic receiver 108 can remain stationary.

Figure 3:
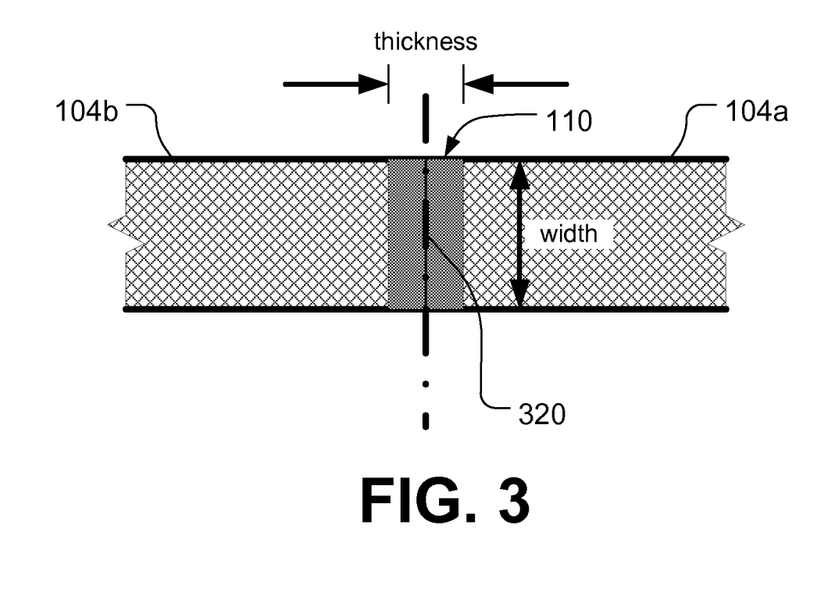
FIG. 3 shows a schematic of a cross-section of an example joint.

FIG. 3 shows a cross-sectional view of example joint 110. In some cases, the joint 110 is a weld such as an electron beam weld, an inertia weld, or another type of joint. The joint 110 defines a joint axis 320 at each location on the joint 110. The width of the joint axis 320 can also be the width of the joint 110. The joint 110 also has a thickness that describes the length the joint 110 extends from both sides of the joint 110 midwall.

Figure 4:
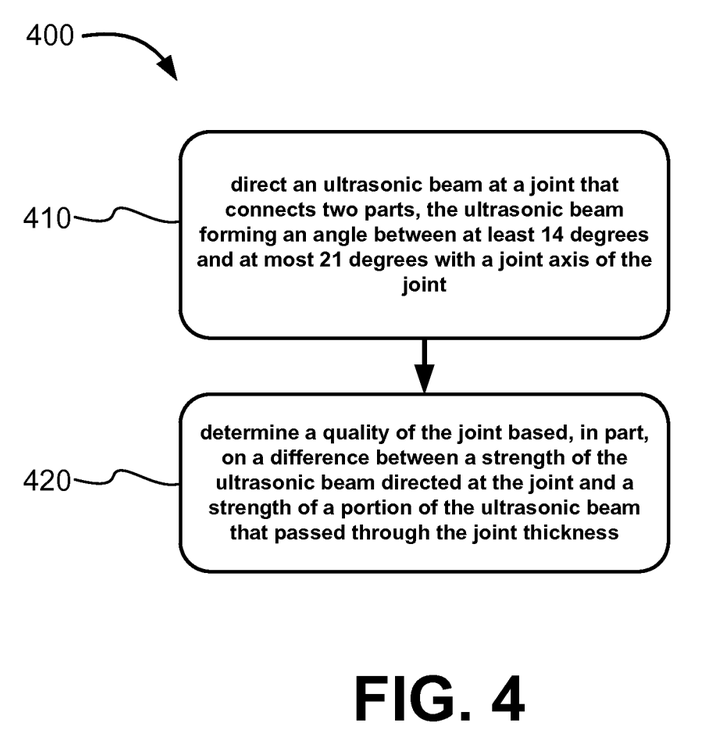
FIG. 4 is a flowchart of an example inspection process that can be implemented by the example inspection system.

FIG. 4 is a flowchart of an example inspection process 400 that can be implemented by example inspection system 100. At 410, an ultrasonic beam is directed at the joint that connects the two parts. The ultrasonic beam is directed at an angle between at least 14 degrees and at most 21 degrees with a joint axis of the joint. In some implementations, the ultrasonic beam transmitter is calibrated relative to the joint before directing the ultrasonic beam at the joint. For example, the position or angle of the ultrasonic beam transmitter can be calibrated. Some characteristics of the ultrasonic beam directed into the joint can also be calibrated. Example characteristics include the strength of the beam, the frequency of the beam, the size of the beam, the shape of the beam, or other characteristics. In some implementations, a calibration joint with one or more defects having known properties is inspected with the ultrasonic beam. The results of the calibrated inspection can be used, for example, to calibrate the ultrasonic beam transmitter or to compare with defects detected in another joint.

At 420, the quality of the joint is determined. For example, defects in the joint can be identified, and the quality of the joint can be determined from the properties of the defects (e.g., size, number, spacing, depth, or other properties). The determination of the quality of the joint can be based, in part, on a difference between a strength of the ultrasonic beam directed at the joint and a strength of a portion of the ultrasonic beam that passed through the joint thickness. The difference can be analyzed to identify defects and thus determine the quality of the joint. For example, defects within the joint can scatter ultrasonic beam energy, and a portion of the scattered energy can be received by an ultrasonic receiver.

The ultrasonic beam can be traversed along a length (i.e., the "scan index") so that the ultrasonic beam is directed at multiple locations on the joint. For example, the ultrasonic beam transmitter can be traversed along a component axis (e.g. component axis 112). Additionally, the component can be rotated or translated to allow multiple locations on the joint to be inspected with the ultrasonic beam. In some implementations, the ultrasonic beam is directed at a first edge of the rectangular width of the joint, and the beam is then traversed from the first edge to a diagonally opposite edge of the joint. Inspecting at multiple locations allows a portion of the joint or the entire joint to be inspected. The quality of multiple locations on the joint can also be determined in the manner described above. In some implementations, a region in the joint is identified through which the ultrasonic beam passed, and the quality of the identified region is determined. For example, a specific location in the joint or a specific cross-sectional area of the joint can be inspected. In other implementations, other types of joint regions or shapes of regions can be inspected. In some implementations, more than one scan is performed with the ultrasonic beam and the portion of the ultrasonic beam that passed through the joint. In some cases, the quality of the joint can be determined from an output of the multiple scans. For example, multiple scans can be used to verify inspection data, reduce signal-to-noise of an inspection measurement, to inspect separate regions of a joint, or for other applications.

Figure 5:
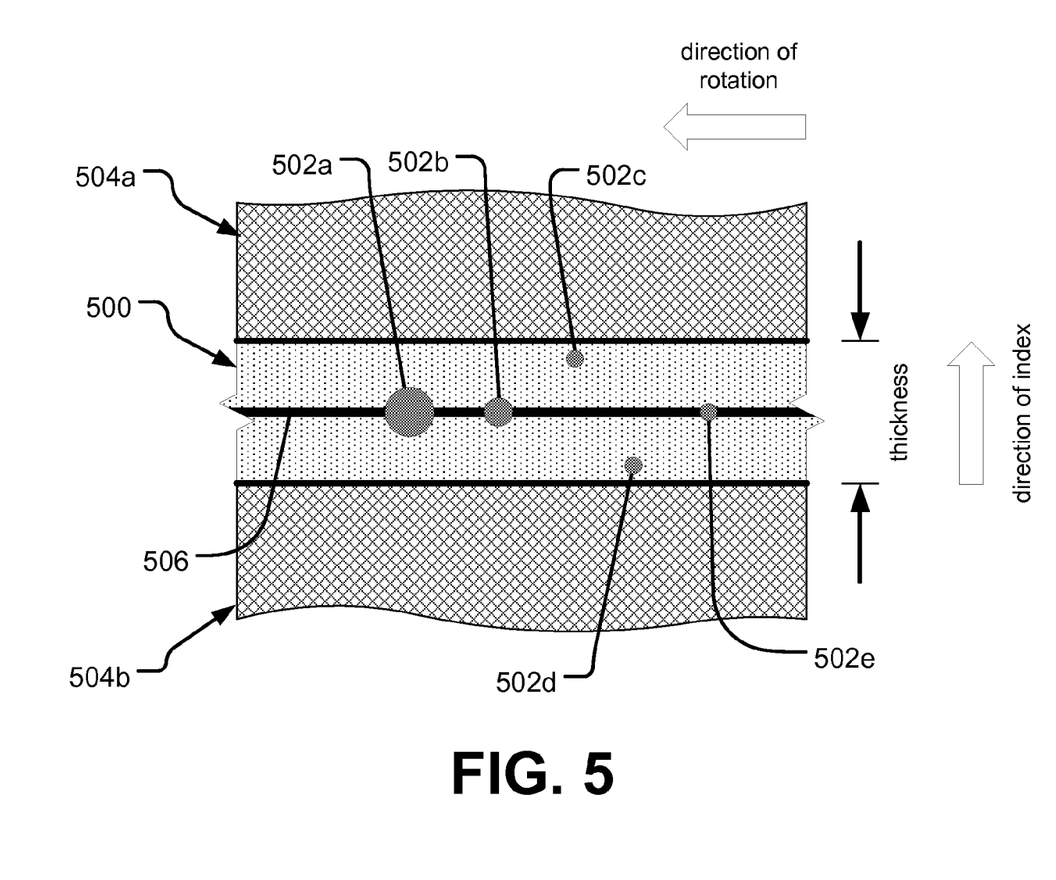
FIG. 5 is a schematic diagram of an example joint.

FIG. 5 shows a schematic diagram of an example joint 500 joining example parts 504*a* and 504*b*. The joint 500 has multiple defects 502*a-e* with different properties that can be determined using example inspection process 400 implementing example inspection system 100. The joint midwall 506 is located approximately in the center of the joint 500. FIG. 5 also has arrows showing an example scan index direction and an example component rotation direction relative to the joint 500. An example defect property that can be determined includes the size of the defect, shown by the different relative sizes of defects 502*a*, 502*b*, and 502*e*. The depth of the defect in the joint 500 can also be determined. For example, defects 502*a*, 502*b*, and 502*e* are located near the midwall 506, but defects 502*c* and 502*d* are located away from the midwall 506 and close to the edge of the thickness of the joint 500. In some cases, the depth of a defect is measured relative to the midwall 506. Multiple defects in a joint can also be identified along a width of the joint, and the spacing between a first defect and a second adjacent defect can be determined. For example, the spacing between defects 502*a* and 502*b* can be determined using the inspection process 400. These are example defect properties; other properties can be determined such as defect shape, defect type, joint roughness, or other properties.

Figure 6:
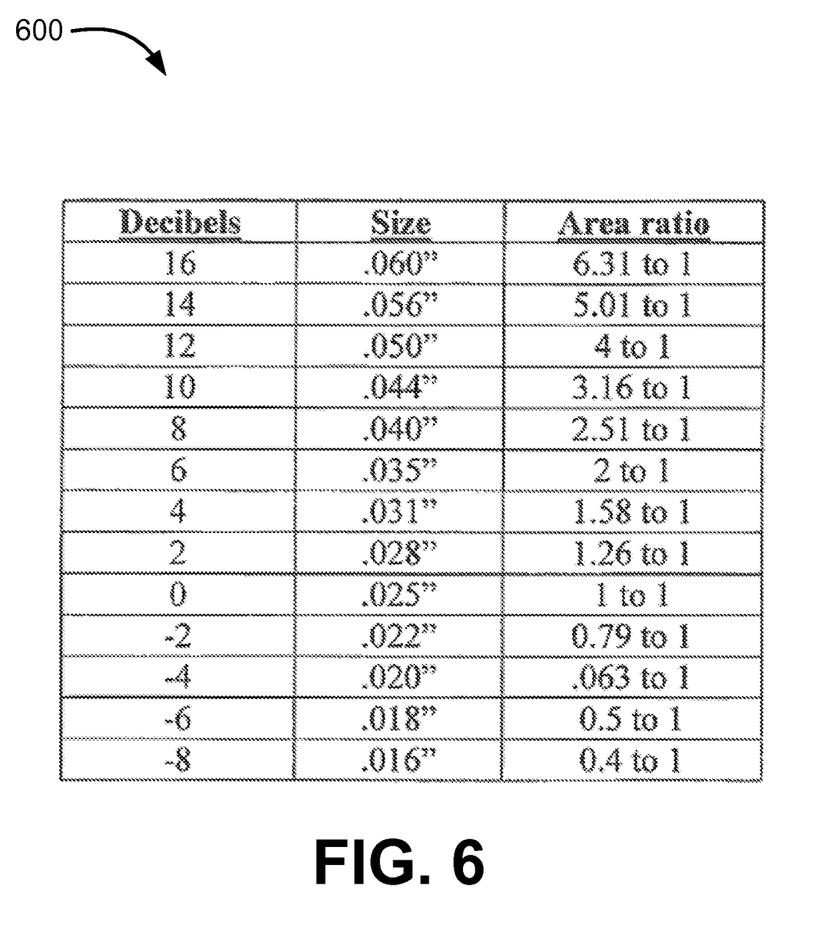
FIG. 6 is an example table that can be used with the steep delta wave technique to approximate defect size.

As an example, the size of a defect can be approximated by comparing the strength of the received scattered energy with the scattered energy from a known calibration defect. FIG. 6 shows an example table 600 that can be used to approximate the size of a hole defect relative to a calibrated hole defect 0.025" in size (i.e., in diameter). For example, if the scattered energy from a measured defect is 6 decibels larger than the scattered energy from a calibrated 0.025" defect (see under "Decibels" column), the table 600 shows that measured defect size is approximately 0.035" in diameter (see under "Size" column), and the measured defect area is approximately twice the area of the calibrated defect (see under "Area ratio" column). Other tables or procedures can be used to characterize defects of different sizes, areas, or other features.

As another example, the distance between an edge of the joint and the location of a defect can be estimated. The distance can be estimated using the equation Edge Distance=(thickness/2)−($D$×1.235)−(size/2)

wherein thickness is the thickness of the joint, D is the distance from the defect to the midwall, and size is the estimated size of the defect. The size size can be obtained, for example, from scattered energy measurements of the defect by using table such as table 600. The distance D can be obtained, for example, from a scan of a portion of the joint, such as shown in FIG. 5.

In some implementations, some of the inspection system 100 or inspection process 400 can be part of a computer system. For example, the computer system can store instructions executable by the computer system to determine the quality of the joint. The computer system can process data from the ultrasonic beam transmitter or ultrasonic beam receiver. The data can include a difference between the strength of the ultrasonic beam directed at the joint and a strength of a portion of the ultrasonic beam that passed through the joint thickness, or the data can include some other information or instructions.

Figure 7:
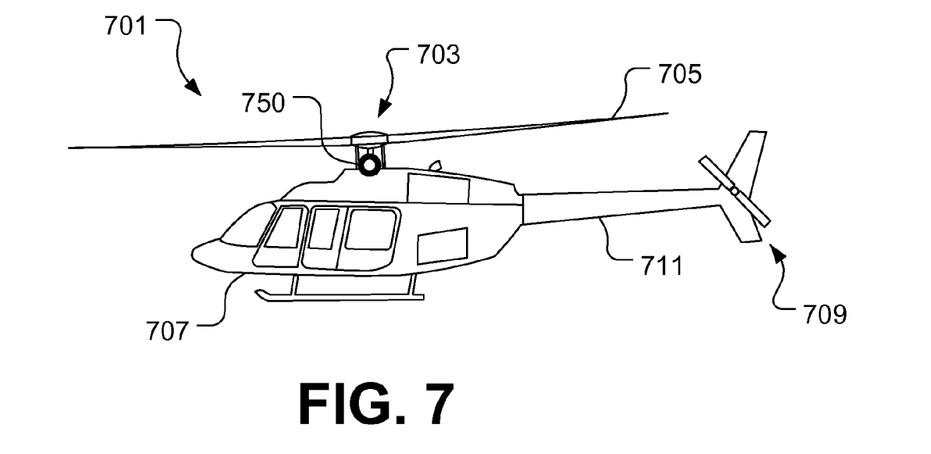
FIG. 7 is a schematic diagram showing an example of a rotorcraft.

The example inspection system 100 can be used to inspect parts for an aircraft. As an example, FIG. 7 shows a schematic diagram of an example rotorcraft 701. Rotorcraft 701 has a rotor system 703 with multiple rotor blades 705. Rotorcraft 701 can further include a fuselage 707, anti-torque system 709, and an empennage 711. The rotorcraft 701 can also include components 750 with joints that can be inspected with inspection system 100. A component 750 is shown in an example location within the transmission of the rotorcraft 701.

Figure 8:
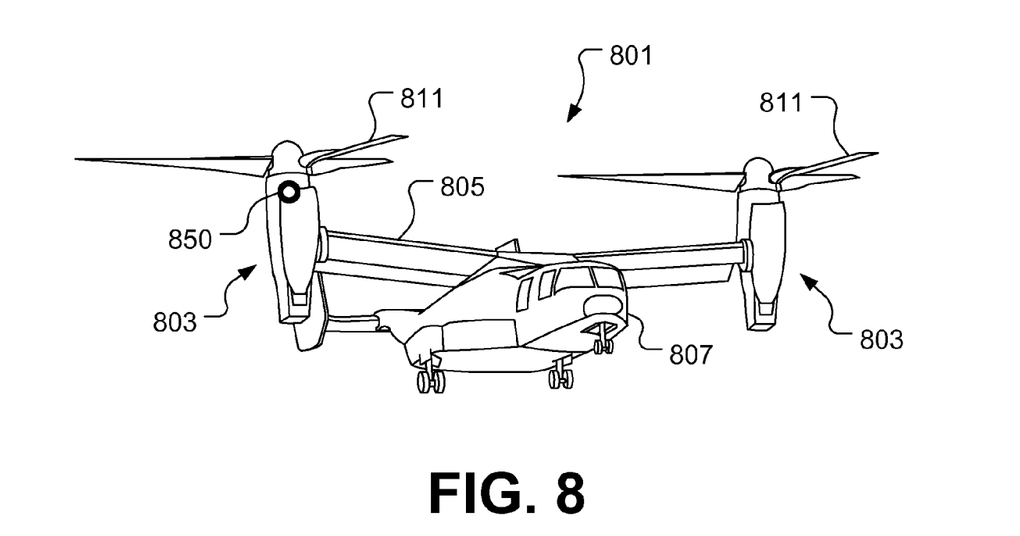
FIG. 8 is a schematic diagram showing an example of a tiltrotor aircraft.

As another example aircraft, FIG. 8 shows a schematic diagram of an example tiltrotor aircraft 801. Aircraft 801 includes a fuselage 807 with attached wings 805. Nacelles 803 are carried at the outboard ends of wings 805 and are rotatable between the helicopter-mode position shown and a forward-facing airplane-mode position (not shown). Nacelles 803 carry engines and transmissions for powering rotor systems 811 in rotation. An engine may be an internal combustion engine, an electrical power source and associated motor, or any other suitable technique for powering rotor system 811. The tiltrotor aircraft 801 can include components 850 that can be inspected with inspection system 100. A component 850 is shown in an example location within a transmission of the tiltrotor aircraft 801.

Thus, particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results

What is claimed is:

1. A method of inspecting a joint that connects two parts, the method comprising:
   directing an ultrasonic beam from an ultrasonic beam transmitter at a joint that connects two parts, the ultrasonic beam forming an angle between at least 14 degrees and at most 21 degrees with a joint axis of the joint, wherein the ultrasonic beam passes through a joint thickness of the joint; and
   determining a quality of the joint based, in part, on a difference between a strength of the ultrasonic beam directed at the joint and a strength of a portion of the ultrasonic beam that passed through the joint thickness.

2. The method of claim 1, wherein the joint has a rectangular width, and wherein directing the ultrasonic beam at the joint comprises:
   directing the ultrasonic beam at a first edge of the rectangular width of the joint; and
   traversing the ultrasonic beam from the first edge to a diagonally opposite edge of the joint.

3. The method of claim 1, wherein directing the ultrasonic beam at the joint comprises directing the ultrasonic beam at a plurality of locations on the joint, and wherein the method further comprises:
   determining a plurality of strengths of the ultrasonic beam at the respective plurality of locations on the joint; and
   determining a plurality of strengths of a plurality of portions of the ultrasonic beam, each portion having passed through the joint thickness at a respective location of the plurality of locations.

4. The method of claim 3, wherein determining the quality of the joint comprises:
   identifying a region in the joint through which the ultrasonic beam directed at a location of the plurality of locations passed; and
   determining a quality of the identified region in the joint based, in part, on a difference between a strength of the ultrasonic beam directed at the location and a strength of a portion of the ultrasonic beam that passed through the joint thickness at the location.

5. The method of claim 1, wherein determining the quality of the joint comprises:
   identifying a defect in the joint based on the difference between the strength of the ultrasonic beam directed at the joint and the strength of the portion of the ultrasonic beam that passed through the joint thickness; and
   determining a depth of the defect in the joint.

6. The method of claim 1, wherein determining the quality of the joint comprises:
   identifying a first defect and a second adjacent defect along a width of the joint based on the difference between the strength of the ultrasonic beam directed at the joint and the strength of the portion of the ultrasonic beam that passed through the joint thickness; and
   determining a spacing between the first defect and the second adjacent defect.

7. The method of claim 1, wherein determining the quality of the joint comprises:
   performing a plurality of scans on the ultrasonic beam and the portion of the ultrasonic beam that passed through the joint; and
   determining the quality of the joint based, in part, on an output of the plurality of scans.

8. The method of claim 1, wherein the joint is an electron beam weld.

9. The method of claim 8, wherein the joint joins a spiral bevel gear of a rotorcraft to a shaft of the rotorcraft.

10. The method of claim 1, further comprising calibrating the ultrasonic beam transmitter relative to the joint before directing the ultrasonic beam at the joint.

11. The method of claim 1, wherein the angle is at least one of 15 degrees or 16 degrees.

12. The method of claim 1, wherein the frequency of the ultrasonic beam directed at the joint is at least 10 MHz.

13. A joint inspection system comprising:
an ultrasonic beam transmitter, the ultrasonic beam transmitter operable to direct an ultrasonic beam at a joint that connects two parts, the ultrasonic beam forming an angle between at least 14 degrees and at most 21 degrees with a joint axis of the joint, the joint axis extending through the width of the joint, wherein the ultrasonic beam passes through a joint thickness of the joint; and
an ultrasonic beam receiver directed towards a location on an opposite end of the joint to the ultrasonic beam transmitter and operable to detect the ultrasonic beam directed by the ultrasonic beam transmitter.

14. The system of claim 13, wherein the ultrasonic beam transmitter is arranged relative to the joint to:
direct the ultrasonic beam at a first edge of the rectangular width of the joint; and
traverse the ultrasonic beam from the first edge to a diagonally opposite edge of the joint.

15. The system of claim 13, further comprising a computer system storing instructions executable by the computer system to determine a quality of the joint based, in part, on a difference between a strength of the ultrasonic beam directed at the joint and a strength of a portion of the ultrasonic beam that passed through the joint thickness.

16. The system of claim 15, wherein directing the ultrasonic beam at the joint comprises directing the ultrasonic beam at a plurality of locations on the joint, and wherein determining the quality of the joint comprises:
determining a plurality of strengths of the ultrasonic beam at the respective plurality of locations on the joint; and
determining a plurality of strengths of a plurality of portions of the ultrasonic beam, each portion having passed through the joint thickness at a respective location of the plurality of locations.

17. The system of claim 16, wherein determining the quality of the joint further comprises:
identifying a region in the joint through which the ultrasonic beam directed at a location of the plurality of locations passed; and
determining a quality of the identified region in the joint based, in part, on a difference between a strength of the ultrasonic beam directed at the location and a strength of a portion of the ultrasonic beam that passed through the joint thickness at the location.

18. The system of claim 15, wherein determining the quality of the joint comprises:
identifying a defect in the joint based on the difference between the strength of the ultrasonic beam directed at the joint and the strength of the portion of the ultrasonic beam that passed through the joint thickness; and
determining a depth of the defect in the joint.

19. The system of claim 15, wherein determining the quality of the joint comprises:
identifying a first defect and a second adjacent defect along a width of the joint based on the difference between the strength of the ultrasonic beam directed at the joint and the strength of the portion of the ultrasonic beam that passed through the joint thickness; and
determining a spacing between the first defect and the second adjacent defect.

20. The system of claim 15, wherein determining the quality of the joint comprises:
performing a plurality of scans on the ultrasonic beam and the portion of the ultrasonic beam that passed through the joint; and
determining the quality of the joint based, in part, on an output of the plurality of scans.

* * * * *